(12) United States Patent
Kim

(10) Patent No.: US 7,156,850 B2
(45) Date of Patent: Jan. 2, 2007

(54) SCREW FOR FIXING SPINE

(76) Inventor: Sung-Kon Kim, 201-304 Hanjin Apartment, #609-1 Donam-dong, Sungbuk-ku Seoul 136-753 (KR)

( * ) Notice: Subject to any disclaimer, the term of this patent is extended or adjusted under 35 U.S.C. 154(b) by 496 days.

(21) Appl. No.: 10/469,898

(22) PCT Filed: Jun. 4, 2001

(86) PCT No.: PCT/KR01/00949

§ 371 (c)(1),
(2), (4) Date: Sep. 5, 2003

(87) PCT Pub. No.: WO02/069854

PCT Pub. Date: Sep. 12, 2002

(65) Prior Publication Data

US 2004/0097926 A1 May 20, 2004

(30) Foreign Application Priority Data

Mar. 6, 2001 (KR) ............................ 2001-05923 U
May 23, 2001 (KR) ............................ 2001-15105 U

(51) Int. Cl.
*A61B 17/56* (2006.01)
(52) U.S. Cl. ...................................................... 606/61
(58) Field of Classification Search ................ 606/73, 606/61
See application file for complete search history.

(56) References Cited

U.S. PATENT DOCUMENTS

| 5,176,680 | A | 1/1993 | Vignaud et al. |
| 5,752,957 | A * | 5/1998 | Ralph et al. ................ 606/61 |
| 5,964,760 | A | 10/1999 | Richelsoph |
| 6,132,432 | A | 10/2000 | Richelsoph |
| 6,440,132 | B1 * | 8/2002 | Jackson ....................... 606/61 |
| 6,485,494 | B1 * | 11/2002 | Haider ......................... 606/73 |
| 6,520,963 | B1 | 2/2003 | McKinley |
| 2003/0125741 | A1 * | 7/2003 | Biedermann et al. ......... 606/61 |

FOREIGN PATENT DOCUMENTS

JP         10-225467         8/1998

OTHER PUBLICATIONS

International Preliminary Examination Report dated May 15, 2003 from PCT Application No. PCT/KR01/00949 filed Jun. 4, 2001.

* cited by examiner

*Primary Examiner*—Eduardo O. Robert
*Assistant Examiner*—Michael J. Araj
(74) *Attorney, Agent, or Firm*—Christie, Parker & Hale, LLP.

(57) ABSTRACT

The present invention relates to a screw assembly for fixing the human spine, in particular, the spine column. The fixing screw assembly uses a cap for fixing a rod arranged in spine implants in order to stabilize the spine column.

14 Claims, 4 Drawing Sheets

[FIG. 1]
(Prior Art)
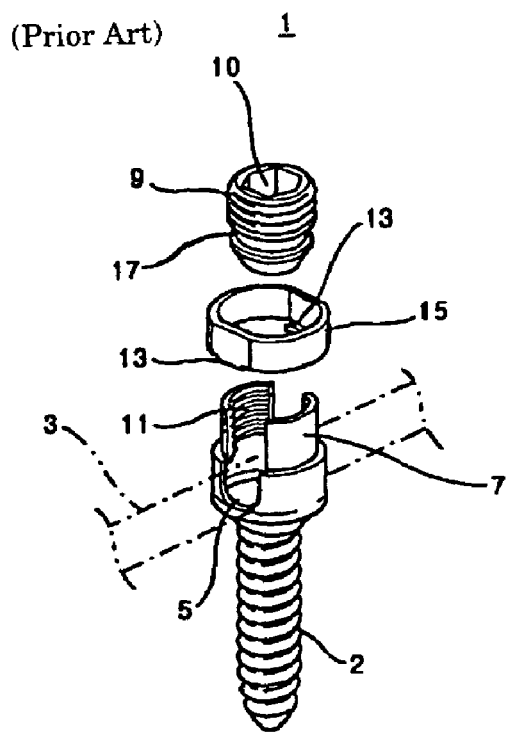
[FIG. 2]
(Prior Art)
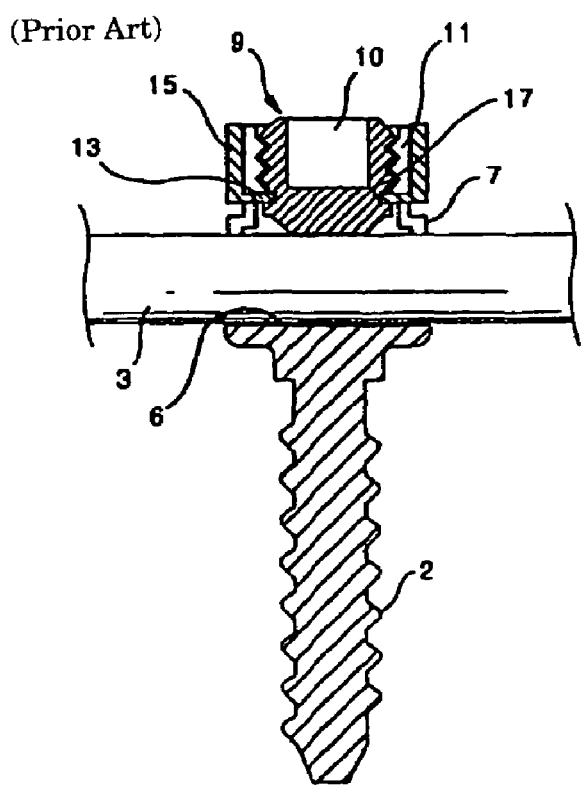

[FIG. 3]
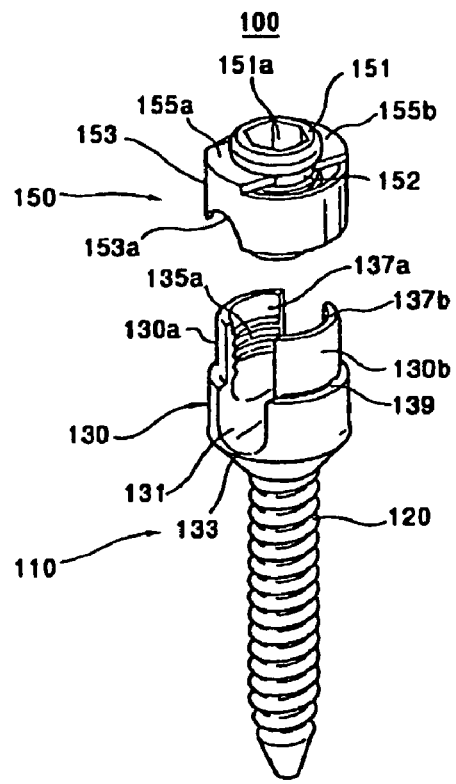
[FIG. 4]
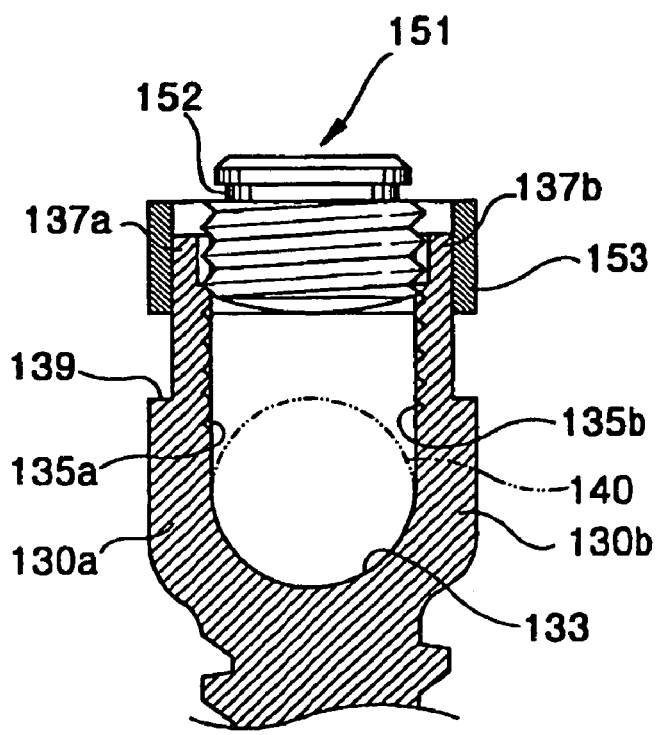

[FIG. 5]
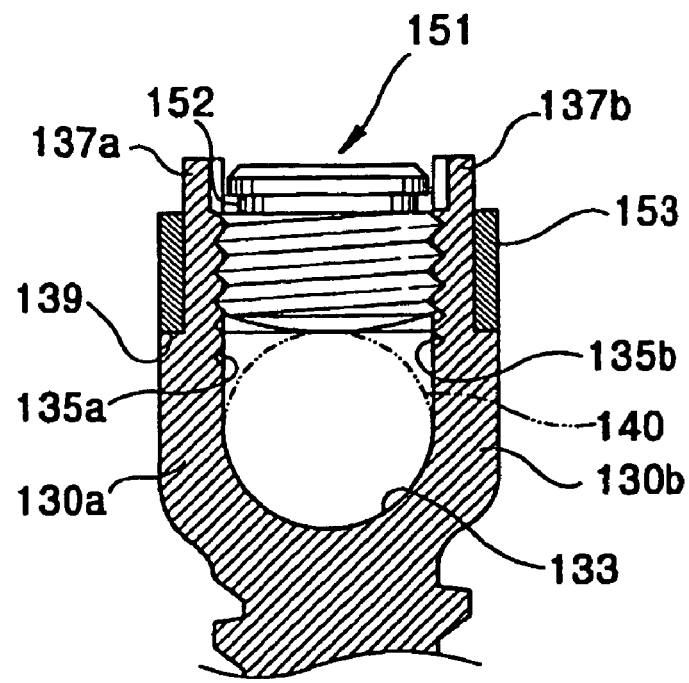
[FIG. 6]
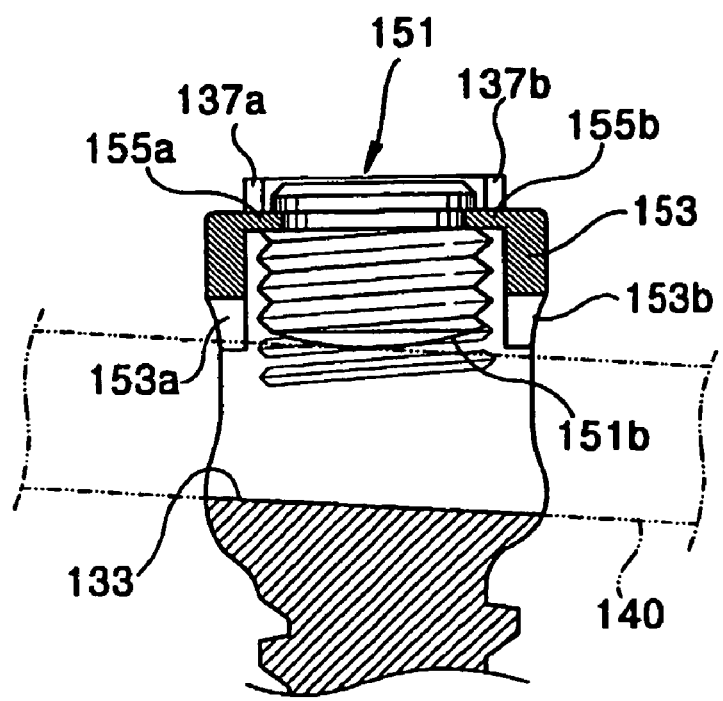

[FIG. 7]
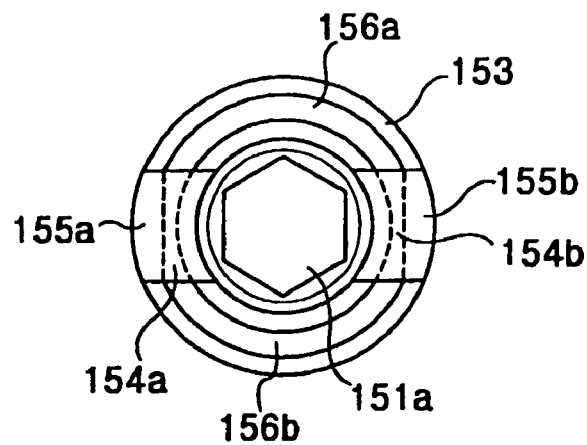
[FIG. 8]
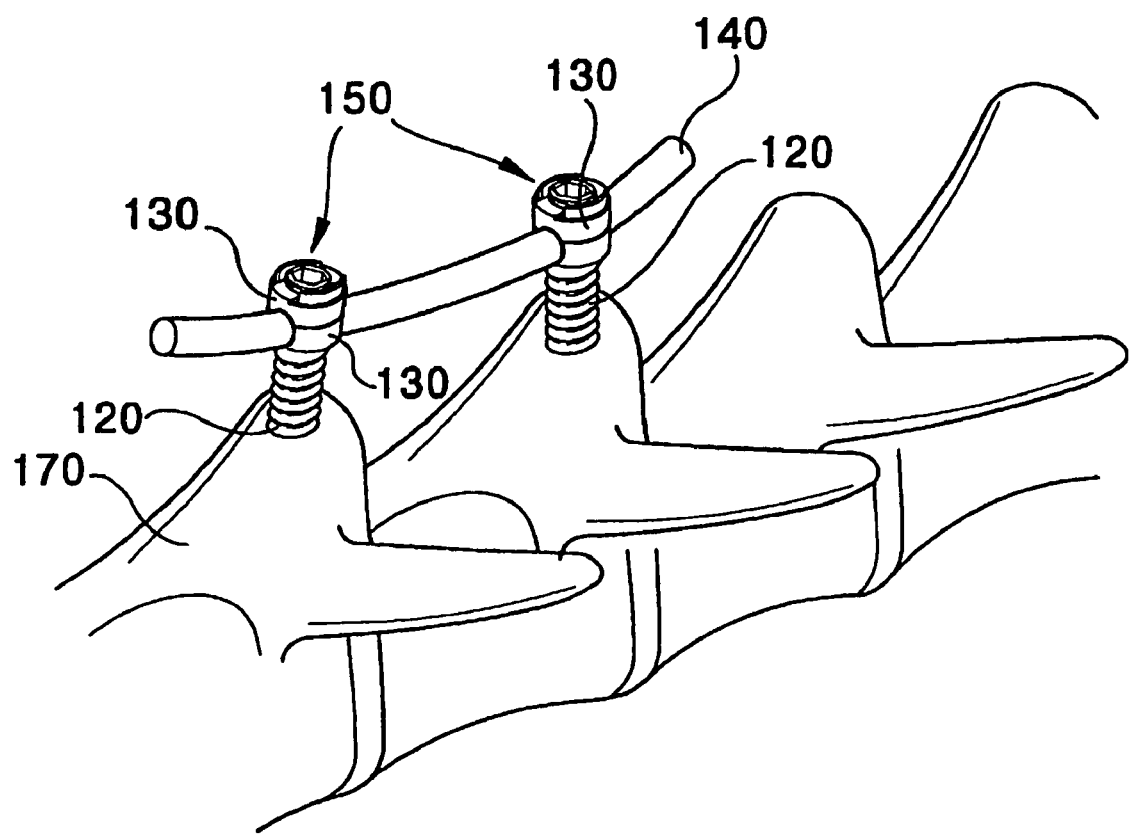

SCREW FOR FIXING SPINE

CROSS-REFERENCE TO RELATED APPLICATION

This application is a National Phase Patent Application of International Application Number PCT/KR01/00949, filed on Jun. 4, 2001, which claims priority of Korean Patent Application Numbers 2001/5923, filed on Mar. 6, 2001 and 2001/15105, filed May 23, 2001.

TECHNICAL FIELD

The present invention relates to a screw assembly for fixing the human spine, in particular, the spine column. The fixing screw assembly uses a cap for fixing a rod arranged in spine implants in order to stabilize the spine column.

BACKGROUND ART

Korean Utility Model Registration No. 175040 filed by the inventor discloses an example of the above device, which is shown in FIGS. 1 and 2.

FIG. 1 is a perspective view illustrating a spine fixing screw assembly disclosed in the above document, and FIG. 2 is a sectional view illustrating the assembled posture of the screw shown in FIG. 1.

As shown in FIGS. 1 and 2, the spine fixing screw assembly 1 has vertical extensions 7 at both sides of a rod receiver 5 for receiving a rod 3. Each of the vertical extensions 7 has a female screw portion 11 for transporting a male screw 9 for fixing the rod 3 received in the rod receiver 5. The spine fixing screw assembly 1 is so configured to transport the male screw 9 via connector members 13 and wrap a rim 15 around the vertical extensions 7.

In the above configuration, the connector members 13 connect between the lower end of the rim 15 and a recess 17 in a lower portion of the male screw 9. The undescribed reference numeral 2 designates a screw, and the reference numeral 10 designates a groove for a wrench.

The spine fixing screw assembly 1 configured as above has the following problems:

First, since threads of the male screw 9 primarily contact with those of the female screws 11 when the male screw 9 is initially engaged into the female screws 11, the central axis of the male screw 9 is hardly aligned with the central axis of the vertical extensions 7 thereby probably prolong the operation time.

Second, the recess 17 is formed adjacent to the lower portion of the male screw 9 so that the male screw 9 is restricted in the number of threads to lower the engaging force.

Third, since the connector members 13 are formed in a lower portion of the rim 15, the connector members 13 primarily contact with the rod 3 if the rod 3 is flexed. Then, the male screw 9 does not sufficiently contact with the rod 3 thereby potentially dropping the fixing force.

Fourth, since the male screw 9 has a flat lower end, if the rod 3 is settled in the rod receiver 5 in a flexed or tilted manner, the contact area is reduced to lower the fixing force of the rod 3.

Fifth, since the rod receiver 5 has a horizontal settling face 6, the rod 3 is not closely contacted with the rod receiver 5 if arranged in a tilted manner in respect to the settling face 6 so as to potentially drop the fixing force thereof.

Sixth, the rim 15 is not further transported downward from the position of fitting thresholds formed in the outer periphery of the vertical extensions 7. In an operation where the rod is necessarily fixed more strongly, the male screw 9 is necessarily subjected to a very strong engaging force. Since the rim 15 has a uniform thickness, the rim 15 may be distorted into an oval shape or radially fractured since an excessive force may be applied to the rim 15 in engagement of the male thread 9.

SUMMARY OF THE INVENTION

According to a another embodiment, the invention is directed to a spine fixation method that includes providing a spine fixing screw assembly as described above, inserting the implant screw into a vertebral body; inserting a rod into the rod receiver of the implant; and tightening the cap onto the implant such that the male screw pressingly engages the rod for fixedly attaching the rod within the rod receiver.

According to a further embodiment, the invention is directed to a spine fixing screw assembly that includes an implant screw for being inserted into a vertebral body; a rod receiver coupled to the implant screw for receiving a rod; at least two vertical extensions coupled to the rod receiver, each vertical extension having an interior threading disposed on a lower surface of the extension and a thread-free upper surface; a coupling screw mateable with the interior threading of the vertical extensions; and a rim having at least two arms horizontally projecting from an upper end of the rim towards a central axis of the rim, an end of each arm being designed to be received in a recess disposed on an upper surface of the coupling screw for rotatably supporting the coupling screw at the central axis of the rim, wherein the vertical extensions are designed to be inserted between the rim and the coupling screw thereby causing the rim to surround an exterior of the vertical extensions and align the central axis of the coupling screw and the central axis of the vertical extensions and further allow the mating of the coupling screw with the interior threading of the vertical extensions.

According to another embodiment, the invention is directed to a spine-fixation method that includes utilizing at least one spine fixing screw assembly as described above to fix at least one vertebral body.

Accordingly, the present invention has been made to solve the foregoing problems and it is an object of the present invention to provide a spine fixing screw assembly having a configuration for reliably fixing a rod received in an implant as well as simply aligning the central axis of a male screw with the central axis of female screws.

According to an aspect of the invention to obtain the above objects, it is provided a spine fixing screw assembly comprising: an implant having an implant screw for being implanted into a spine and a pair of vertical extensions with a rod receiver and female screws; and a cap for being coupled with said implant, wherein said cap comprises a male screw for screwing with said female screws to fix a rod, a rim for surrounding the exterior of said vertical extensions and a pair of connector members each with one side being projected from the upper end of said rim and the other end being received in a recess provided in said male screw, whereby said male screw is rotatably supported in respect to said rim and the number of threads of the male screw can be increased, and wherein said vertical extensions each are provided in the upper ends with insert guides for being inserted between said rim and said male screw to align the central axis of said male screw and the central axis of said vertical extensions.

In the spine fixing screw assembly, said rim is preferably provided in the inner periphery with flat portions opposed in parallel to each other to prevent the rim from skidding.

In the spine fixing screw assembly, each of said connector members is projected from the upper end of said rim having said flat portions and said vertical extensions are vertically longer than said rim so as to reliably guide projection of the insert guides as the rod is fixed.

In the spine fixing screw assembly, recesses each are provided in the lower end of said rim having said flat portions so as to more reliably maintain contact between the lower end of the male screw and the rod.

In the spine fixing screw assembly, said male screw has an arc-shaped lower end for contacting with said rod so as to increase a contacting area with the rod received as tilted.

In the spine fixing screw assembly, said rod receiver is tilted so as to enhance contact with the rod even though the implants are irregular in height since they are installed where the spine is flexed.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a perspective view of a spine fixing screw assembly precedently filed by the inventor;

FIG. 2 is a sectional view of the screw shown in FIG. 1 in its assembled state;

FIG. 3 is a perspective view of a spine fixing screw assembly according to a preferred embodiment of the invention;

FIG. 4 is a sectional view of the spine fixing screw assembly in FIG. 3 in an initially assembled stage which is taken along the radial direction of a rod;

FIG. 5 is sectional view of the spine fixing screw assembly in FIG. 4 which is completely assembled;

FIG. 6 is a sectional view of the spine fixing screw assembly in FIG. 3 in its assembled state which is taken along the longitudinal direction of the rod;

FIG. 7 is a plan view of a cap of the spine fixing screw assembly; and

FIG. 8 is a perspective view of the spine fixing screw assembly in use.

REFERENCE NUMERALS OF IMPORTANT PARTS OF THE DRAWINGS

100: spine fixing screw assembly
110: implant
150: cap
120: screw
130: head
130a, 130b: vertical extension
131: rod receiver
133: settling face
135a, 135b: female screw
137a, 137b: insert guide
139: fitting threshold
140: rod
150: cap
151: male screw
151a: wrench groove
151b: male screw lower end
152: bridging recess
153: rim
153a, 153b: rod receiving recess
154a, 154b: flat portion
155a, 155b: connector member
156a, 156b: gap
170: spine column

BEST MODE FOR CARRYING OUT THE INVENTION

The following detailed description will disclose a preferred embodiment of the present invention in reference to the accompanying drawings.

FIG. 3 is a perspective view of a spine fixing screw assembly according to a preferred embodiment of the invention, FIG. 4 is a sectional view of the spine fixing screw assembly in FIG. 3 in an initially assembled stage which is taken along the radial direction of a rod, FIG. 5 is sectional view of the spine fixing screw assembly in FIG. 4 which is completely assembled, FIG. 6 is a sectional view of the spine fixing screw assembly in FIG. 3 in its assembled state which is taken along the longitudinal direction of the rod, FIG. 7 is a plan view of a cap of the spine fixing screw assembly, and FIG. 8 is a perspective view of the spine fixing screw assembly in use.

As shown in FIGS. 3 to 8, a spine fixing screw assembly 100 according to the preferred embodiment of the invention comprises two major components such as an implant 110 and a cap 150.

In the above configuration, the implant 110 is constituted of a head 130 and an implant screw 120 for being fixedly inserted into a spine or spine column 170.

The head 130 includes a pair of vertical extensions 130a and 130b bounded by U-shaped grooves. The head 130 has a rod receiver 131 for receiving a rod 140 between the vertical extension 130a and 130b. When the spine column subjected to implantation is bent (as the spine or spine column is usually bent), a plurality of implants 110 implanted into the spine column may be ununiform in height. Then, the rod 140 is installed as tilted to drop the adhering force between the rod 140 and the rod receiver 131 so that the rod 140 cannot be securely fixed. In order to overcome this, the rod receiver 131 is provided with a tilted settling face 133. The settling face 133 preferably has a tilt angle set as about 5 to 20°, preferably 10°.

The vertical extensions 130a and 130b are provided in their internal periphery with female screws 135a and 135b for receiving a male screw 15i for fixing the rod 140 settled in the rod receiver 131. Further, the vertical extensions 130a and 130b have insert guides 137a and 137b each formed in upper portions thereof, more particularly, connected to the upper ends of the female screws 135a and 135b for aligning the central axis of the male screw 151 with the central axis of the female screws 135a and 135b. That is, as shown in FIGS. 3 and 4, the insert guide 137a and 137b having no threads unlike the female screws 135a and 135b are inserted between a rim 153 of the cap 150 and the male screw 151. Therefore, the insert guides 137a and 137b are so structured that the exteriors of the insert guides 137a and 137b are surrounded by a portion of the rim 135 while the interiors of the insert guides 137a and 137b receive the male screw 151. Due to the initial engaging structure, as shown in FIG. 4, the male screw 151 and the rim 153 are installed as supported to the insert guides 137a and 137b of the vertical extensions 130a and 130b. Therefore, in operation, an operator readily install the cap 150 in the implant 110 as well as easily align the central axis of the male screw 151 with the center of the female screws 135a and 135b. The operator can easily engage the cap 150 into the implant 110 without any misalignment by turning the male screw 151 in this state. Therefore, the operation can be performed in a simple and correct manner.

In particular, the central axis of the male screw 151 is aligned with the center of the vertical extensions 130a and 130b as the rim 153 is supported to the insert guides 137a and 137b. Therefore, the rim 153 is preferably provided vertically longer (that is, in a portion for surrounding the vertical extensions) than the lead (i.e. the length of the threads) of the male screw 151 (that is, to have a configuration that the lower end of the rim 153 is projected downward beyond the lower end of the male screw).

Further, the insert guides 137a and 137b each are so configured to project through gaps 156a and 156b between the rim 153 and the male screw 151 when the rod 150 is fixed by the male screw 151. Therefore, even though the insert guides 137a and 137b are provided, the threads of the male screw 151 are not reduced in number thereby maintaining a proper degree of engaging force as it is. This can be obtained by introducing the insert guides 137a and 137b of the vertical extensions 130a and 130b to easily project from the upper ends of the rim 153 by means of the flat portion 154a, 154b, that is, vertical extensions 130a and 130b provided, in particular, in portions combining the female screws 135a and 135b and the insert guides 137a and 137b, longer than the rim 153.

The vertical extensions 130a and 130b are provided in the outer periphery with fitting thresholds 139 for butting against the lower end of the rim 153 to prevent any further downward movement of the rim 153. If the thresholds 139 are not provided when the rod 140 is small in diameter, the male screw 151 may pass a boundary portion between the rod receiver 131 and the female screws 135a and 135b to reduce the number of engaged threads thereby weakening the engaging force. The thresholds 139 are installed in the boundary portion between the rod receiver 131 and the female screws 135a and 135b to prevent weakening of the engaging force. It is apparent, of course, the female screws 135a and 135b can be extended into the inner wall of the rod receiver 131 rather than installing the thresholds 139.

The cap for fixing the rod 140 is mainly constituted of the male screw 151, the rim 153 and connector members 155a and 155b.

The male screw 151 functions to move through thread-engagement into the female screws to fix the rod 140. The male screw 151 is provided in an upper portion with a wrench groove 151a for allowing the male screw 151 to be easily turned. The lower end 151b of the male screw 151 contacting with the rod 140 can be shaped flat or into a concave arc or convex arc. If convex arc-shaped, the lower end 151b can enhance the fixing force by enlarging a contacting area even though the rod is flexed and thus supported in a tilted manner.

The rim 153, as set forth above, is so configured to stably secure the central axis of the male screw 153 in the initial engagement stage while surrounding the exterior of the vertical extensions 130a and 130b to prevent any opening of the vertical extensions 130a and 130b after engagement. Therefore, the vertical extensions 130a and 130b each are arranged in the gaps 156a and 156b between the inner wall of the rim 153 and the threads of the male screw 151. Further, the rim 153 is provided in the lower end with a pair of rod receiving recesses 153a and 153b opposed to each other. The rod receiving recesses 153a and 153b may be configured according to the sectional configuration of the rod 140. Since the rod has a circular sectional configuration, the rod receiving recesses 153a and 153b each are preferably shaped as semi-circles. The rod receiving recesses 153a and 153b are necessarily installed in a position identical with the U-shaped groove of the rod receiver 131 to receive the rod 140. For the purpose of this, the rim 153 has flat portions 154a and 154b. That is, the flat portions 154a and 154b each are formed by partially varying the thickness of the rim 153. For instance, as shown in FIG. 7, the flat portions 154a and 154b can be produced by thickening the rim 153 in portions corresponding to positions where the rod receiving recesses 153a and 153b are installed than in other portions (corresponding to positions where the gaps 156a and 156b are formed). This causes gaps between the flat portions 154a and 154b and the male screw 151 to be smaller than the thickness of the vertical extensions 130a and 130b, by which the vertical extensions 130a and 130b are so introduced to be always inserted between the gaps 156a and 156b. Therefore, even though the male screw 151 is turned, the rim 153 is not rotated due to interaction between the flat portions 154a and 154b and the vertical extensions 130a and 130b so as to correctly locate the rod receiving recesses 153a and 153b to the U-shaped groove of the rod receiver 131.

As above, since the flat portions 154a and 154b are supported as inserted into the vertical extensions 130a and 130b and prevent rotation of the rim 153 when the cap 150 is initially installed in the implant 110, the operator can automatically locate the rod receiving recesses 153a and 153b to the U-shaped groove of the rod receiver 131 by simply turning the male screw 153 without gripping the rim 153. Therefore, the operation can be performed easily and conveniently.

Further, as set forth above, the flat portions 154a and 154b are relatively thicker than other portions to have a relatively excellent strength than the thinner portions. This can alleviate the rim 153 from distortion or fracture even though the male screw 151 strongly presses against the rod 140 to more securely fix the rod 140. The rim 153 stably surrounds the outer periphery of the vertical extensions 130a and 130b to securely fix the rod 140.

The connector members 155a and 155b are components functioning to construct the rim 153 and the male screw 151 into a unitary body having the same axis, and constituted of a pair of arms 155a and 155b. Each of the arms 155a and 155b is horizontally projected by one side from the upper end of the rim 153 while being received by the other side in a circular bridging recess 152 which is provided in an upper portion of the male screw 151. The bridging recess 152 allows the male screw 151 to relatively rotate in respect to the rim 153 as well as the rim 153 moves along the exterior of the vertical extension 130a and 130b to surround the same as the male screw is transported to the female screws 135a and 135b. The bridging recess 152 is provided in the upper portion of the male screw 151 so that the entire threads of the male screw 151 can be engaged at least into the female screws 135a and 135b. The connector members 155a and 155b each are provided at positions opposed to the rod receiving recesses 153a and 153b. Then, the flat portions 154a and 154b each introduce the vertical extensions 130a and 130a, in particular, the insertion guides 137a and 137b, is guided between the gap 156a and 156b to reliably project from the upper end of the rim 153.

Various modifications, additions and substitutions can be made to the spine fixing screw assembly of the invention without departing from the technical scope and spirit of the invention.

INDUSTRIAL APPLICABILITY

As set forth above, the spine fixing screw assembly of the invention has the following effects.

First, since the vertical extensions are provided with the insert guides for receiving and supporting the male screw by their interiors while supporting the rim surrounded around the same by their exteriors, the operator can align the central axis of the male screw with the center of the vertical extensions while simply installing the cap in the implant. This allows rapid and correct engagement thereby to reduce the operation time.

Second, the connector members are provided in the upper portion for connecting between the rim and the recess of the male screw to increase the threads of the male screw in number thereby enhancing the engaging force of the male screw.

Third, the rim is provided in the inner periphery with the thick flat portions opposed to each other. The flat portions prevent rotation of the rim in respect to the rotation of the male screw so that the male screw is smoothly transported to reduce the engaging time. Further, the rim is alleviated from distortion or fracture even, though the male screw strongly presses against the rod. So, the rod can be reliably fixed.

Fourth, the connector members each are projected from the upper end of the rim having the flat portions to securely guide the positions within the insert guides.

Fifth, the vertical extensions are vertically longer than the rim so that the threads of the male screws can be maintained in number even though the insert guides are formed.

Sixth, the recesses are provided at the lower end of the rim having the flat portions so that the recesses are located to the groove of the rod receiver. Further, even though the flexed rod is received in the rod receiver, the rod is received in the recesses while the contacting area between the male screw and the rod can be increased. This allows the male screw to securely fix the rod.

Seventh, the lower end of the male screw is shaped as a convex arc so as to increase the contacting area between the male screw and the flexed or tilted rod.

Eighth, since the settling face of the rod receiver is tilted, the rod can be closely fixed to the rod receiver even though the rod is arranged as tilted.

The invention claimed is:

1. A spine fixing screw assembly comprising:
   an implant having an implant screw for being implanted into a spine and a pair of vertical extensions with a rod receiver and female screws; and
   a cap for being coupled with said implant,
   wherein said cap comprises a male screw for screwing with said female screws to fix a rod, a rim for surrounding the exterior of said vertical extensions and a pair of connector members each with one side being projected from the upper end of said rim and the other end being received in a recess provided in said male screw, whereby said male screw is rotatably supported in respect to said rim, and
   wherein said vertical extensions each are provided in the upper ends with insert guides for being inserted between said rim and said male screw to align the central axis of said male screw and the central axis of said vertical extensions.

2. The spine fixing screw assembly according to claim 1, wherein said rim is provided in the inner periphery with flat portions opposed in parallel to each other.

3. The spine fixing screw assembly according to claim 2, wherein each of said connector members is projected from the upper end of said rim having said flat portions, wherein said vertical extensions are vertically longer than said rim.

4. The spine fixing screw assembly according to claim 2 or 3, further comprising recesses each provided in the lower end of said rim having said flat portions.

5. The spine fixing screw assembly according to claim 1, wherein said male screw has an arc-shaped lower end for contacting with said rod.

6. The spine fixing screw assembly according to claim 1, wherein said rod is receiver is tilted.

7. The spine fixing screw assembly of claim 1, wherein the implant screw and the vertical extensions comprise a single unit.

8. A spine fixation method comprising:
   providing a spine fixing screw assembly as described in claim 1;
   inserting the implant screw into a vertebral body;
   inserting a rod into the rod receiver of the implant; and
   tightening the cap onto the implant such that the male screw pressingly engages the rod for fixedly attaching the rod within the rod receiver.

9. A spine fixation method comprising utilizing at least one spine fixing screw assembly as described in claim 1 to fix at least one vertebral body.

10. A spine fixing screw assembly comprising:
    an implant screw for being inserted into a vertebral body;
    a rod receiver coupled to the implant screw for receiving a rod;
    at least two vertical extensions coupled to the rod receiver, each vertical extension having an interior threading disposed on a lower surface of the extension and a thread-free upper surface;
    a coupling screw mateable with the interior threading of the vertical extensions; and
    a rim having at least two arms horizontally projecting from an upper end of the rim towards a central axis of the rim, an end of each arm being designed to be received in a recess disposed on an upper surface of the coupling screw for rotatably supporting the coupling screw at the central axis of the rim, wherein the vertical extensions are designed to be inserted between the rim and the coupling screw thereby causing the rim to surround an exterior of the vertical extensions and align the central axis of the coupling screw and the central axis of the vertical extensions and further allow the mating of the coupling screw with the interior threading of the vertical extensions, wherein the thread-free upper surface of the vertical extensions are designed to project vertically beyond an upper end of the rim through a gap disposed between the two arms when the vertical extensions are inserted between the rim and the coupling screw.

11. The spine fixing screw assembly of claim 10, wherein the rim includes a rod receiving recess disposed at a lower end of the rim.

12. The spine fixing screw assembly of claim 10 further comprising a fitting threshold disposed at a lower end of each vertical extension to prevent further downward movement of the rim when the vertical extension is inserted between the rim and the coupling screw.

13. The spine fixing screw assembly of claim 10, wherein the implant screw, the rod receiving channel, and vertical extensions comprise a single unit.

14. A spine fixation method comprising utilizing at least one spine fixing screw assembly as described in claim 10 to fix at least one vertebral body.

* * * * *